(12) United States Patent
Munk

(10) Patent No.: US 9,910,002 B2
(45) Date of Patent: Mar. 6, 2018

(54) DRY RUNNING DETECTION SYSTEM

(71) Applicant: GRUNDFOS HOLDING A/S, Bjerringbro (DK)

(72) Inventor: Flemming Munk, Viborg (DK)

(73) Assignee: GRUNDFOS HOLDING A/S, Bjerringbro (DK)

( * ) Notice: Subject to any disclaimer, the term of this patent is extended or adjusted under 35 U.S.C. 154(b) by 519 days.

(21) Appl. No.: 14/483,353

(22) Filed: Sep. 11, 2014

(65) Prior Publication Data

US 2015/0070036 A1 Mar. 12, 2015

(30) Foreign Application Priority Data

Sep. 12, 2013 (EP) ..................................... 13184065

(51) Int. Cl.
*G01R 27/08* (2006.01)
*G01N 27/06* (2006.01)
*F04D 15/02* (2006.01)
*G01N 29/032* (2006.01)

(52) U.S. Cl.
CPC ......... *G01N 27/06* (2013.01); *F04D 15/0218* (2013.01); *G01N 29/032* (2013.01)

(58) Field of Classification Search
CPC .. G01N 27/06; G01N 29/032; G01F 23/2962; G01F 23/2961; G01F 29/2965; G01F 29/296; G01F 29/28; G01F 15/063; G01F 15/16
See application file for complete search history.

(56) References Cited

U.S. PATENT DOCUMENTS

| 4,144,517 | A | 3/1979 | Baumoel | |
| 4,881,873 | A * | 11/1989 | Smith | F04B 49/025 417/12 |
| 7,615,954 | B1 * | 11/2009 | Potter | G01F 23/296 318/291 |
| 2003/0063985 | A1 * | 4/2003 | Keilman | F04B 17/00 417/322 |
| 2004/0187569 | A1 * | 9/2004 | Rollwage | G01F 23/2962 73/290 V |
| 2010/0090023 | A1 * | 4/2010 | Ricciardi | A61L 2/22 239/102.2 |
| 2011/0085917 | A1 * | 4/2011 | Ward | F04D 13/16 417/36 |
| 2011/0238013 | A1 * | 9/2011 | Wang | A61M 5/16831 604/123 |
| 2014/0165703 | A1 * | 6/2014 | Wilt | G01N 29/02 73/24.06 |

(Continued)

FOREIGN PATENT DOCUMENTS

EP 0 843 100 A1 5/1998
EP 1 510 698 A2 3/2005

*Primary Examiner* — Thang Le
(74) *Attorney, Agent, or Firm* — McGlew and Tuttle, PC

(57) ABSTRACT

The dry running detection system for a pump includes an ultrasonic transducer (8) designed for arrangement inside a pump housing (24) and electrically connected to a frequency generator (2) producing an electrical signal having a predefined frequency. An analyzing unit (10) of the system analyzes the electrical signal applied to the ultrasonic transducer (8) and is designed to detect whether the ultrasonic transducer (8) is in contact with a liquid or not on basis of the signal level of the electrical signal.

20 Claims, 2 Drawing Sheets

(56) References Cited

U.S. PATENT DOCUMENTS

| | | | |
|---|---|---|---|
| 2014/0191054 A1* | 7/2014 | Hingley | A61M 11/005 239/1 |
| 2015/0013646 A1* | 1/2015 | Qi | G01F 23/263 123/478 |
| 2015/0323373 A1* | 11/2015 | Maguin | G01N 29/024 73/290 V |

* cited by examiner

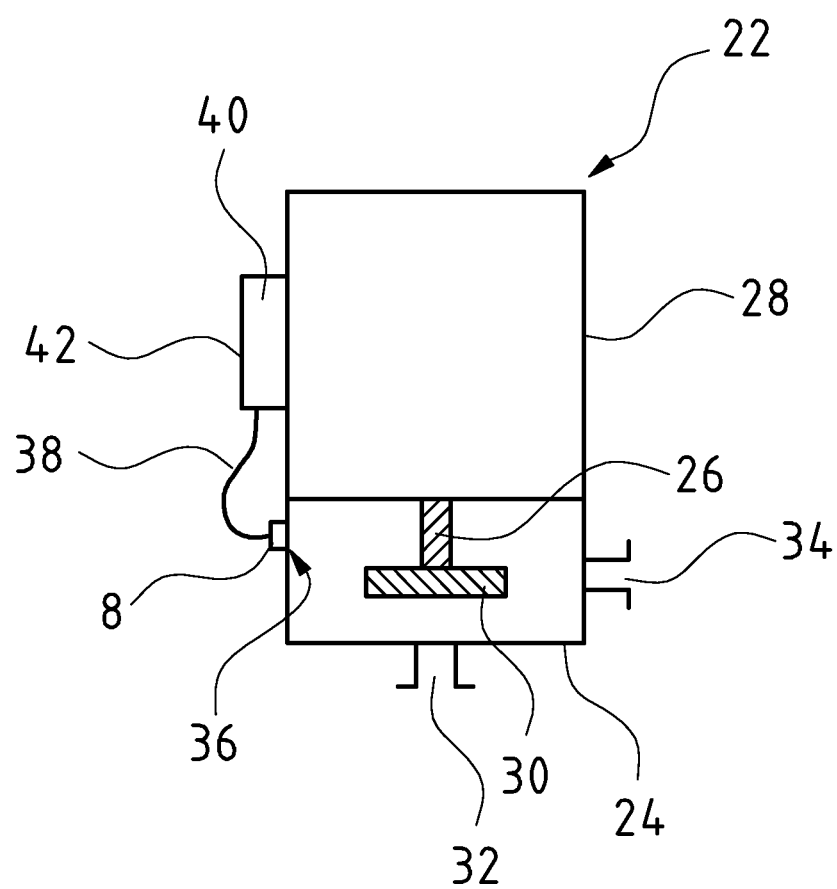

DRY RUNNING DETECTION SYSTEM

CROSS REFERENCE TO RELATED APPLICATIONS

This application claims the benefit of priority under 35 U.S.C. § 119 of European Patent Application EP 13 184 065.4 filed Sep. 12, 2013, the entire contents of which are incorporated herein by reference.

FIELD OF THE INVENTION

The present invention relates to a dry running detection system for a pump, as well as to a pump assembly.

BACKGROUND OF THE INVENTION

Known for protecting pumps against dry running is to measure the electrical conductivity between the pump housing of the pump and the liquid to be pumped. Without liquid, there exists no electrically conductive contact to the pump housing, and there is an extreme rise in resistance. The disadvantage to such measuring systems is that the electrical contact greatly depends on the electrical conductivity of the liquid, and that it most often takes a certain period of time to detect dry running.

Known from EP 1 510 698 A2 is an oscillating fork arranged in a tube flange on the pump for detecting the dry running of a pump. The oscillating fork is made to oscillate at regular intervals. If the oscillating fork is only in contact with air, the oscillation has a longer decay time than when the oscillating fork is in contact with water given the low attenuation. The disadvantage to this design is that an additional tube flange must be secured to the pump to provide enough space for the oscillating fork. In addition, excitation here takes place at a low frequency. As a result, it may be necessary to determine the decay time with several excitations, so as to thereby be able to prevent the excitation from exerting an influence on dry running detection itself.

SUMMARY OF THE INVENTION

Therefore, an object of the invention is to provide a device that enables a quick detection of dry running in a pump in the pump housing given a compact structural design.

The device according to the invention for the detection of dry running in a pump exhibits an ultrasonic transducer, which is designed for accommodation in a pump housing, and electrically connected with a frequency generator for generating an electrical signal with a predefined frequency, as well as an analyzing unit, which analyzes the electrical signal being applied to the ultrasonic transducer, and is designed to detect whether or not there is contact between the ultrasonic transducer and a liquid based on the signal level of the electrical signal. The ultrasonic transducer is designed to convert electrical oscillations into mechanical oscillations. The oscillating frequency here lies in the ultrasonic range. If the ultrasonic transducer is in contact with air, it can oscillate with little attenuation at its excitation frequency. It here exhibits certain electrical features, such as for example a certain impedance. The term impedance here denotes the complex resistance, wherein only the real part of the impedance can be considered here. If the ultrasonic transducer is in contact with a liquid, preferably water, part of the mechanical oscillating energy is released to the water. The oscillation is thereby attenuated, which triggers a change in the oscillating behavior of the ultrasonic transducer. This change can be gauged against the specific electrical features on the ultrasonic transducer. For example, the impedance of the ultrasonic transducer can change as a result.

The analyzing unit is designed to evaluate the electrical signal applied to the ultrasonic transducer. To this end, it has electronic components designed to detect whether or not the ultrasonic transducer is in contact with a liquid based on the electrical signal or change in the electrical signal. According to the invention, the electrical circuits of the analyzing unit are designed in such a way that they can analyze the signal level of the measured electrical signal, and detect from the signal level whether or not the ultrasonic transducer is in contact with a liquid.

The mechanical oscillation of the ultrasonic transducer in the ultrasound region is not audible to the human ear. In addition, at an oscillation period of about 50 µs or below, the ultrasound oscillation is so fast that changes in contact between the ultrasonic transducer and liquid can be detected quickly enough. Dry running can be detected by analyzing the electrical signal for a change in the electrical features of the ultrasonic transducer.

The ultrasonic transducer is preferably designed to be arranged in the pump housing of the pump. To this end, it preferably has a structure small enough to allow it to come into contact with liquids in the interior space of the pump housing, and not impair the pumping action of the pump.

The ultrasonic transducer preferably exhibits a plane surface, which can come into contact with liquids when in the installed position. The plane surface forms a uniform contact surface. This plane surface advantageously abuts flush against an enveloping interior side of the pump housing, so that the ultrasonic transducer itself does not project into the interior space of the pump housing.

It is further preferred that the ultrasonic transducer exhibit a thread, with which it can be screwed together with the pump housing, in particular in a liquid-tight manner. As a consequence, the ultrasonic transducer can be secured to a pump housing which has a corresponding receptacle in the form of a thread, in particular a threaded hole. This makes the ultrasonic transducer easy to change out. It is especially preferred that the thread be designed in such a way that the ultrasonic transducer can be screwed into an opening already present on the pump housing, for example a vent hole, with a corresponding mating thread. As a result, the ultrasonic transducer can be an upgrade part for a pump.

The frequency generator is designed to generate an electrical signal with a predefined frequency. This electrical signal is routed to the ultrasonic transducer, and converted into a mechanical oscillation with the predefined frequency. As a consequence, the ultrasonic frequency of the ultrasonic transducer is equal to the predefined frequency of the electrical signal.

The analyzing unit is electrically connected with the ultrasonic transducer in such a way that it can measure and analyze a decreasing electrical signal level on the ultrasonic transducer. In addition, the analyzing unit is designed to detect whether or not the ultrasonic transducer is in contact with a liquid based on the electrical signal, and in particular based on the change in the electrical signal over time. To this end, the analyzing unit analyzes the signal level or change in the signal level, for example the voltage drop on the ultrasonic transducer or the phase of the electrical signal. For example, when properly configured, the analyzing unit can detect dry running based on the amplitude of the voltage on the ultrasonic transducer reaching or not reaching a predefined value, wherein the predefined value lies between the value given full contact between the ultrasonic transducer and a liquid and the value at which there is no contact between the ultrasonic transducer and a liquid.

In an especially preferred embodiment, the predefined frequency of the electrical signal of the frequency generator lies between 20 kHz and 80 kHz, preferably at 40 kHz. The ultrasonic transducer preferably exhibits a natural frequency in the ultrasonic range. Therefore, it is advantageous for the electrical signal which it converts into a mechanical oscillation in the ultrasonic range to also exhibit a frequency in the kHz or MHZ range. The frequency of the electrical signal here lies between 20 kHz and 80 kHz. The oscillation is not audible to the human ear within this range. In addition, frequency generators for generating frequencies are inexpensive and technically stable in this middle kHz range. The electrical signal preferably exhibits a frequency identical to the natural frequency of the ultrasonic transducer. As a consequence, the ultrasonic transducer can be made to oscillate by the electrical signal without any higher losses. For example, technically cost-effective ultrasonic transducers exhibit a natural frequency of 40 kHz.

The analyzing unit is preferably designed to evaluate an electrical signal whose frequency lies below the ultrasonic range. As already stated, it is technically advantageous to analyze signal changes in a time interval lying above the period of the electrical signal itself, and at which small fluctuations and changes in contact between the ultrasonic transducer and liquid do not have to be detected. For example, a dirt particle may briefly become attached to the ultrasonic transducer, which in this way leads to a rapid change in the specific electrical features of the ultrasonic transducer, wherein the electrical features quickly return back to their initial values after the dirt particle has once again detached itself from the ultrasonic transducer.

It is especially preferred that the analyzing unit be designed to evaluate an electrical DC voltage signal. As a consequence, the analyzing unit does not analyze the signal level of a periodically changing signal, but rather analyzes and detects the current actual value or isolated, persistent changes in the electrical signal to be measured of the kind caused by the dry running of a pump, and hence by a suddenly arising, yet lasting change in one of the electrical features of the ultrasonic transducer. Periodic changes are not acquired. Based on whether the predefined value is dipped below or exceeded, the analyzing unit preferably detects whether or not the ultrasonic transducer is in contact with the liquid.

It is especially preferred that an envelope detector be electrically connected between the ultrasonic transducer and analyzing unit. The envelope detector is used to filter the signal envelope out of the signal that changes over time. As a consequence, at least periodic segments above a certain frequency are filtered out. However, all periodic segments of the electrical signal can also be filtered, thereby leaving behind a DC voltage or direct current signal. Such an envelope detector is advantageously used to filter out precisely those segments of the signal that are not necessary for detecting the dry running of the pump. What remains is a signal that especially lacks periodic changes in the ultrasonic range, and essentially reflects how the amplitude of the electrical signal to be evaluated progresses over time. In addition, the change in signal level caused by the loss of contact between the ultrasonic transducer and liquid can be easily analyzed based on this filtered signal. The analyzing unit is designed to analyze the signal filtered through the envelope detector, and detect whether or not the ultrasonic transducer is in contact with the liquid. As described above, it does so by analyzing the signal level of the filtered signal and comparing it with a predefined value and/or analyzing the change in the signal level over time. The signal level can preferably increase as contact is lost between the ultrasonic transducer and liquid. However, it can also decrease.

The electrical signal of the frequency generator is preferably a square wave signal. A square wave signal is distinguished by its transition steepness during the transition from one amplitude to the next. The ultrasonic transducer converts the electrical square wave signal into a mechanical oscillation having the same frequency.

It is especially preferred that a microcontroller be provided that acts as a frequency generator and/or analyzing unit. The microcontroller is preferably configured in such a way as to output the electrical signal with the predefined frequency. To this end, it preferably has an output for outputting the electrical signal, in particular with a frequency in the kHz range. The microcontroller can further preferably exhibit an input for the electrical signal tapped from the ultrasonic transducer. In addition, the microcontroller is preferably designed to analyze the signal tapped at the ultrasonic transducer, and, within the meaning of the invention, detect whether or not the ultrasonic transducer is in contact with a liquid based on the signal level or change in the signal level. A microcontroller reduces the number of components, since it can preferably handle several functions. In particular, the microcontroller is preferably configured to carry out all necessary operations for analyzing the electrical signal as described in the invention.

The microcontroller is preferably electrically connected to a display, to at least one indicator light or to a speaker or acoustic signaler. In this way, the dry running detection system can be designed to signal the detection of dry running. For example, the connected display can be used to visually depict a graphic image of the dry running. An indicator light, for example an LED, can signal the detection of dry running with a visual warning by lighting up and/or changing color. Alternative or additionally, the dry running detection system can exhibit a loudspeaker, for example, which sends out an acoustic warning signal upon detecting a dry running pump. These output options allow the operator to protect the pump against damage caused by dry running, for example by shutting it down.

In an especially preferred embodiment, the frequency generator and ultrasonic transducer are electrically connected in series to a resistor. The frequency generator sends out an electrical signal, which descends on the resistor and on the ultrasonic transducer. The serial connection between the resistor and ultrasonic transducer yields a voltage divider. Depending on the impedances of the resistor and ultrasonic transducer, a respective voltage drop arises on each of the two components. As a consequence, the signal tapped by the analyzing unit just at the ultrasonic transducer and not at the resistor depends not only on whether or not the ultrasonic transducer is in contact with a liquid, but also on the impedance ratio between the resistor and ultrasonic transducer. In addition, it is advantageous that the resistor prevents a short-circuit at the frequency generator, for example given an extremely low impedance of the ultrasonic transducer.

The invention further relates to a pump assembly with a pump housing, which exhibits a dry running detection system according to the preceding description, wherein the ultrasonic transducer of the system is arranged inside the pump housing in such a way that the ultrasonic transducer can come into contact with a liquid inside the pump housing. The ultrasonic transducer is preferably arranged in the pump assembly, for example a centrifugal pump, in such a way that it can come into contact with a liquid inside the pump housing on the one hand, but does not impede the pump action of the pump on the other. To this end, it preferably does not project into the interior of the pump or into its flow paths, or does so only to a very slight extent. It preferably comprises a portion of the interior wall of the pump housing, i.e., a wall bordering the flow path, wherein it can also be somewhat recessed or extend out in relation to the interior wall within the meaning of the invention. It is especially preferred that the surface of the ultrasonic transducer facing the mounting direction be flush with the interior wall of the pump housing. The ultrasonic transducer is here preferably located in a position inside the pump housing in which contact between the ultrasonic transducer and liquid is lost early on given a dry running pump if important pump parts, like shaft bearings and seals, which can be damaged by dry running, have not been adequately lubricated by the liquid.

It is especially preferred that the ultrasonic transducer exhibits a plane surface with which it comes into contact with a liquid or not. As a consequence, the plane surface best constitutes part of the ultrasonic transducer, which faces into the interior of the pump housing. The surface normal of the plane surface here faces into an interior space of the pump housing, and the plane surface of the ultrasonic transducer preferably itself comprises part of the interior wall of the pump housing that borders the flow path. The ultrasonic transducer in the pump is advantageously liquid-tight and secured so that it can be detached again, in particular screwed in. The pump preferably exhibits a terminal or opening that is open toward the interior space of the pump housing. The ultrasonic transducer exhibits a housing, which is preferably screwed to the terminal of the pump housing by way of a thread, or can be screwed into an opening in the pump housing. As a consequence, if the ultrasonic transducer exhibits a defect, it can be easily unscrewed from the pump again and repaired or replaced with a new one. Within the meaning of the invention, the connection between the pump housing and ultrasonic transducer can also be designed in some other way, for example as a bayonet coupling or clamp mounting.

At least the frequency generator and analyzing unit are preferably spaced apart from the ultrasonic transducer, and in particular arranged in an electronic housing outside the pump housing. The electronic housing preferably incorporates the frequency generator and analyzing unit in a manner protected against splashing water. A cable, possibly with several internal conductors, or several cables, preferably lead from the electronic housing to the ultrasonic transducer, thereby establishing the electrical connection between the ultrasonic transducer and electrical components. The electronic housing preferably contains all electrical components of the dry running detection system except for the ultrasonic transducer. Depending on the embodiment of the invention, the electronic housing can thus accommodate a resistor for serial connection with the ultrasonic transducer as described above, an envelope detector and/or other electrical components. Components in the electronic housing can be easily replaced or repaired, for example if defective. Another advantage to the separate arrangement of the ultrasonic transducer is that it requires little space, and can thus be readily integrated into a pump. In addition, even more components can be introduced into the electronic housing. The dry running detection electronics can be connected with other electronics present in the electronic housing, for example, such as engine control electronics, for purposes of integration into the motor controller of the pump assembly.

The pump housing and/or electronic housing are especially advantageously designed to allow an upgrade to be made to a dry running detection system. The ultrasonic transducer can preferably be designed in such a way that it can be screwed into a present opening in a pump housing, e.g., a vent hole. The electronic housing can form an added component that can be arranged on the pump housing. The electronics of the dry running detection system can thus be situated in the electronic housing as described above.

The electronic housing can preferably incorporate a microcontroller, which takes over the functions of the analyzing unit and function generator. The number of parts is reduced as a result, thereby simplifying assembly of the electrical components in the electronic housing. In addition, the microcontroller can be electrically connected with a display, at least one indicator light and/or a tone generator in or on the electronic housing. As a consequence, the microcontroller can visually or audibly signal the detection of dry running. If technically feasible, the microcontroller, which is present in an electronic housing of the pump assembly for other purposes, can be used to take over the functions of the frequency generator and analyzing unit.

It is especially preferred that a protection unit can be electrically connected with the dry running detection system and drive motor or integrated therein, wherein the protection unit is designed to switch off the drive motor given a dry running of the pump. If the analyzing unit determines that the ultrasonic transducer is no longer in contact with a liquid, so that the pump is running dry, the protection unit is activated, and switches off the drive motor of the pump. While the pump assembly motor can here be switched off by simply interrupting the power supply, a deactivation sequence can also take place, for example to controllably shut down the motor. The protection unit can be preferably connected with the described microcontroller, or included in the microcontroller configuration. As a consequence, the microcontroller handles not just the tasks of the frequency generator and analyzing unit, but also assumes the function of the protection unit, and can switch off the pump when dry running is detected. In the simplest case, the protection unit can consist of a switch, e.g., a relay, but also be realized by having the dry running detection system and motor controller interact in such a way that the motor controller switches off the motor in the event of dry running.

The protection unit is preferably arranged in an electronic housing on the pump housing. At least one of the electronic assemblies listed above can here also be situated in the electronic housing, e.g., parts of the dry running detection system and/or motor controller, wherein the protection unit is electrically connected with the dry running detection system and motor controller electronics, or with the power supply for the motor of the pump connection.

The invention will be explained in greater detail below based on the exemplary embodiments shown in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

FIG. 2 is a schematic longitudinal sectional view of a centrifugal pump assembly with a dry running detection system according to FIG. 1.

DESCRIPTION OF THE PREFERRED EMBODIMENTS

Figure 1:
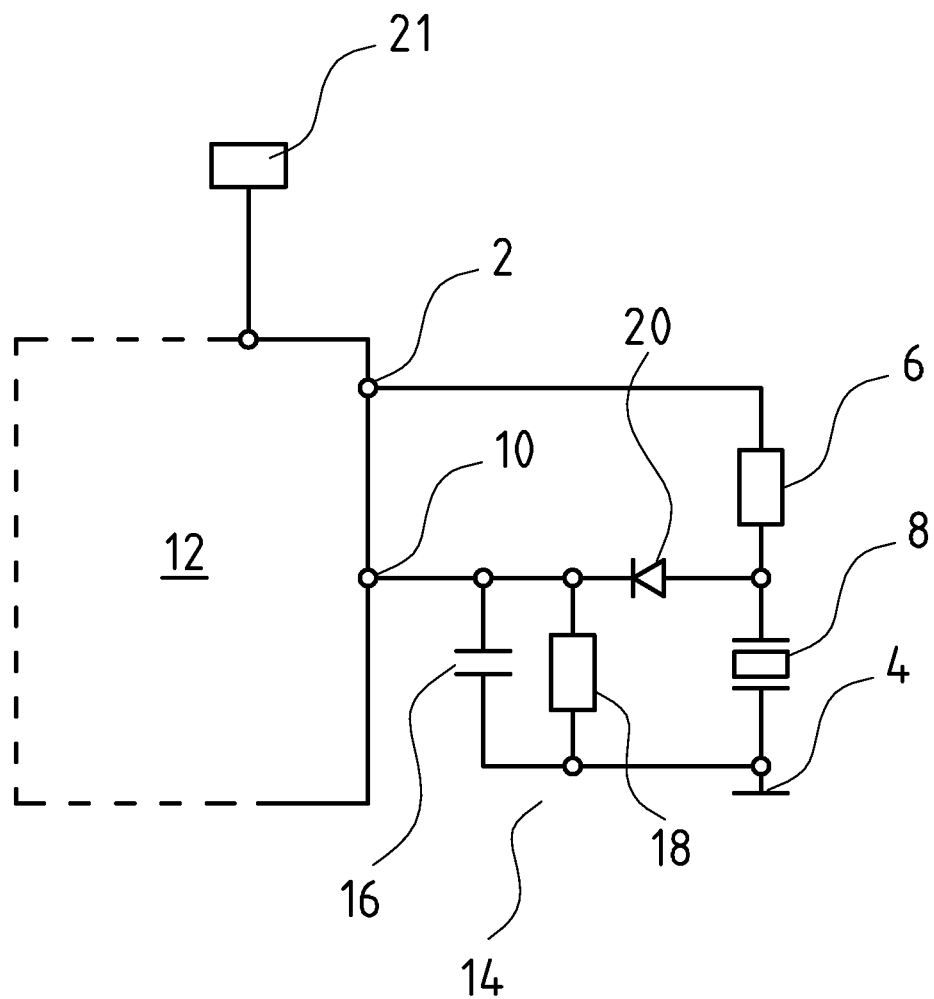
FIG. 1 is a schematic circuit diagram of the dry running detection system according to the invention.

Referring to the drawings in particular, the system according to the schematic circuit diagram presented on FIG. 1 exhibits a microcontroller 12, which comprises a frequency generator and an analyzing unit, i.e., assumes their functions. To this end, it has a frequency generator output 2 and an analyzing unit input 10. A series connection consisting of a first ohmic resistor 6 and an ultrasonic transducer 8 is set up between the frequency generator output 2 and a reference potential 4 predefined by the microcontroller 12. The analyzing unit input 10 is electrically connected with the ultrasonic transducer 8.

A signal with a predefined frequency of about 40 kHz is generated at the frequency generator output 2 in relation to the reference potential 4, and descends as a function of the impedance ratio between the first ohmic resistor 6 and the ultrasonic transducer 8, with the voltage being correspondingly divided on the first ohmic resistor 6 and the ultrasonic transducer 8. The portion of the electrical signal that descends on the ultrasonic transducer 8 is converted by the ultrasonic transducer 8 into a mechanical oscillation, which also exhibits a frequency of about 40 kHz.

In terms of analyzing unit function, the microcontroller 12 is designed to evaluate the part of the electrical signal tapped at the ultrasonic transducer 8 and applied to the analyzing unit input 10 in such a way that the microcontroller 12 detects whether or not the ultrasonic transducer 8 is in contact with a liquid. If the ultrasonic transducer 8 is in contact with a liquid, for example water, its mechanical oscillation is attenuated by the liquid more strongly that if it were in contact with a gas, for example air. This elevated attenuation of the ultrasonic transducer 8 manifests itself in an elevated voltage level on the ultrasonic transducer 8. As a consequence, a higher signal portion can be tapped on the ultrasonic transducer 8 by comparison to contact with air. The analyzing unit of the microcontroller 12 is designed to detect the level or level magnitude of the signal portion or the change therein. If the microcontroller 12 acts as the analyzing unit to evaluate the voltage amplitude of the electrical signal descending on the ultrasonic transducer 8, it will detect a high voltage drop given contact between the ultrasonic transducer 8 and a liquid. If the pump is running dry, i.e., the ultrasonic transducer 8 loses contact with the liquid or is no longer in contact with the liquid, the measured voltage drops.

An envelope detector 14 is arranged between the analyzing unit input 10 and the ultrasonic transducer 8. In this example, the envelope detector 14 consists of a capacitor 16, a second ohmic resistor 18, which are situated parallel to the ultrasonic transducer 8 between the analyzing unit input 10 and reference potential 4, and a diode 20, which is arranged in a mesh with the parallel circuit of the capacitor 16 and second ohmic resistor 18 and the ultrasonic transducer 8. The diode 20 is arranged in the forward direction.

The envelope detector 14 is designed in such a way that the analyzer unit input 10 has applied to it a signal that is based upon the voltage drop on the ultrasonic transducer 8, and which at least no longer exhibits any high-frequency portions in the kHz range or above. The diode 20 in this case ensures that the positive signal portion is allowed through and that the high-frequency portions are then filtered out of the signal via the parallel circuit comprised of the capacitor 16 and second ohmic resistor 18. As a consequence, the analyzing unit input 10 in this case only relays to the microcontroller 12 a signal whose changes in amplitude signal over time are essentially based on whether or not the ultrasonic transducer 8 is in contact with a liquid.

In addition, in this example the microcontroller 12 is electrically connected with a protection unit 21, which is designed to switch off the pump assembly motor. As a consequence, a pump assembly motor can be switched off by means of the protection unit 21 when dry running is detected. However, this is not a feature compulsory for the invention.

FIG. 2 presents a schematic view of an exemplary embodiment for a pump assembly in the form of a centrifugal pump assembly 22 with the dry running detection system according to the invention. The centrifugal pump assembly 22 exhibits a shaft 26 in its pump housing 24. The shaft 26 is driven by a motor in a motor housing 28. An impeller 30 is arranged on the shaft 26 in the pump housing 24. However, several impellers 30 can also be arranged on the shaft 26. The pump housing 24 exhibits a suction connection 32 and pressure connection 34 in a known manner.

An electronic housing 40 is arranged on the motor housing 28. The electronic housing 40 incorporates motor electronics used to control the centrifugal pump assembly 22.

The ultrasonic transducer 8 is screwed into an opening 36 in the pump housing 24 by means of a thread. The ultrasonic transducer 8 is connected with the electronic housing 40 by means of an electrical cable 38, which runs outside the pump housing 24. As depicted on the schematic circuit diagram on FIG. 1, the electronic housing 40 incorporates the envelope detector 14 and a first ohmic resistor 6 as part of the electronics in addition to the microcontroller 12, wherein the ultrasonic transducer 8 is electrically connected with the components in the electronic housing 40 by means of the cable 38 according to FIG. 1. The microcontroller 12 registers whether or not contact exists with the liquid to be pumped at the location inside the pump housing 24 where the ultrasonic transducer 8 is situated. The ultrasonic transducer 8 is designed in such a way that it can preferably be screwed into a vent opening in the pump housing 24. This makes it simple to upgrade existing pump assemblies.

The electronic housing 40 exhibits a display 42 that is arranged on the exterior side of the electronic housing 40, and designed at least to indicate whether or not dry running was detected by the microcontroller 12. The display 42 is electrically connected with the microcontroller 12. The display 42 can also indicate other data, for example the speed and run time of the centrifugal pump assembly 22. Aside from the display 42, at least one LED can alternatively or additionally be situated in the electronic housing 40, and be electrically connected with the microcontroller 12. As a consequence, the microcontroller 12 is able to indicate via the LED whether or not it has registered a dry running of the centrifugal pump assembly 22.

In order to protect the centrifugal pump assembly 22 against dry running, in this example the microcontroller 12 is connected with the protection unit 21 of the motor also situated in the electronic housing 40 in such a way that the motor in the motor housing 28 can be switched off by the protection unit 21 given the detection of a dry running centrifugal pump assembly 22. This makes it possible to prevent a dry running centrifugal pump assembly 22 from damaging a bearing and the impeller 30 on the shaft 26, for example. However, the invention may be carried out without such protection unit 21.

In this example, the protection unit 21 is integrated into the motor control electronics of the centrifugal pump assembly 22. During assembly of the electronic housing 40, the protection unit 21 is also built in as part of the motor control electronics of the centrifugal pump assembly 22. In an alternative embodiment, the protection unit 21 can be designed as an added component, which can be situated in the electronic housing 40 or in its own electronic housing, and electrically connected with the motor or motor control electronics. This makes it possible to upgrade an already mounted centrifugal pump assembly 22 with a dry running safeguard, or the dry running safeguard can be modularly integrated into the centrifugal pump assembly 22 as an option.

While specific embodiments of the invention have been shown and described in detail to illustrate the application of the principles of the invention, it will be understood that the invention may be embodied otherwise without departing from such principles.

APPENDIX:
Reference list

| | | | |
|---|---|---|---|
| 2 | Frequency generator output | 32 | Suction connection |
| 4 | Reference potential | 34 | Pressure connection |
| 6 | First ohmic resistor | 36 | Port |
| 8 | Ultrasonic transducer | 38 | Cable |
| 10 | Analyzing unit input | 40 | Electronic housing |
| 12 | Microcontroller | 42 | Display |
| 14 | Envelope detector | | |
| 16 | Capacitor | | |
| 18 | Second ohmic resistor | | |
| 20 | Diode | | |
| 21 | Protection unit | | |
| 22 | Centrifugal pump assembly | | |
| 24 | Pump housing | | |
| 26 | Shaft | | |
| 28 | Motor housing | | |
| 30 | Impeller | | |

What is claimed is:

1. A dry running detection system, comprising:
a pump comprising a pump housing;
an electronic housing arranged outside the pump housing;
a frequency generator producing an electrical signal having a predefined frequency;
an ultrasonic transducer arranged inside said pump housing and electrically connected to the frequency generator; and
an analyzing unit comprising electronic components configured to analyze the electrical signal applied to the ultrasonic transducer and configured to detect whether the ultrasonic transducer is in contact with a liquid in the pump housing or not on basis of the signal level of the electrical signal, wherein the frequency generator and the analyzing unit are arranged in the electronic housing.

2. The dry running detection system according to claim 1, wherein the predetermined frequency of the electrical signal of the frequency generator is between 20 kHz and 80 kHz.

3. The dry running detection system according to claim 2, wherein the predetermined frequency of the electrical signal of the frequency generator is at or near 40 kHz.

4. The dry running detection system according to claim 1, wherein the analyzing unit is designed to analyze the electrical signal with a frequency below a predetermined ultrasonic frequency.

5. The dry running detection system according to claim 4, wherein the analyzing unit is designed to analyze the electrical signal, the electrical signal being an electrical DC signal.

6. The dry running detection system according to claim 1, wherein an envelope detector is electrically connected between the ultrasonic transducer and the analyzing unit.

7. The dry running detection system according to claim 1, wherein the electrical signal produced by the frequency generator is a square wave.

8. The dry running detection system according to claim 1, wherein at least one of:
the frequency generator is comprised by a microcontroller that provides the frequency generator function; and
the analyzing unit is comprised by the microcontroller.

9. The dry running detection system according to claim 8, further comprising at least one of a display, an indicator light and/or a speaker, wherein the microcontroller is electrically connected to at least one of the display, the indicator light and the speaker.

10. The dry running detection system according to claim 1, wherein the frequency generator and the ultrasonic transducer are electrically connected to a resistance in series.

11. A pump assembly comprising:
a pump housing; and
a dry running detection system comprising:
a frequency generator producing an electrical signal having a predefined frequency;
an ultrasonic transducer designed for arrangement inside the pump housing and electrically connected to the frequency generator; and
an analyzing unit comprising electronic components configured to analyze the electrical signal applied to the ultrasonic transducer and configured to detect whether the ultrasonic transducer is in contact with a liquid or not on basis of the signal level of the electrical signal, wherein the ultrasonic transducer of the dry running detection system is arranged inside the pump housing such that the ultrasonic transducer can make contact with the liquid inside the pump housing, wherein the frequency generator and the analyzing unit are arranged in an electronic housing which is arranged outside the pump housing.

12. The pump assembly according to claim 11, further comprising a protection unit electrically connected to the dry running detection unit and connected to a drive motor of the pump, wherein the protection unit switches off the drive motor when detecting the dry running of the pump by the dry running detection system.

13. The pump assembly according to claim 11, wherein the predetermined frequency of the electrical signal of the frequency generator is between 20 kHz and 80 kHz.

14. The pump assembly according to claim 11, wherein the analyzing unit analyzes the electrical signal with a frequency below a predetermined ultrasonic frequency level.

15. The pump assembly according to claim 11, wherein the analyzing unit analyzes the electrical signal, the electrical signal being an electrical DC signal.

16. The pump assembly according to claim 11, wherein an envelope detector is electrically connected between said ultrasonic transducer and said analyzing unit.

17. The pump assembly according to claim 11, wherein at least one of:
said frequency generator is comprised by a microcontroller that provides said frequency generator function; and
said analyzing unit is comprised by said microcontroller.

18. The pump assembly according to claim 17, further comprising:
   at least one of a display, an indicator light and/or a speaker, wherein the microcontroller is electrically connected to at least one of the display, the indicator light and the speaker.

19. A dry running detection system, comprising:
   a pump assembly comprising a pump, said pump comprising a pump housing, said pump housing comprising a pump housing inlet, a pump housing outlet, a fluid interior space and an impeller interior space, at least a portion of said fluid interior space receiving a fluid;
   an impeller arranged in said impeller interior space;
   an electronic housing arranged outside the pump housing;
   a frequency generator producing an electrical signal having a predefined frequency;
   an ultrasonic transducer positioned for operating within an interior of one or more of said impeller interior space and said fluid interior space, said ultrasonic transducer being electrically connected to said frequency generator; and
   an analyzing unit comprising a microcontroller configured to analyze said electrical signal applied to said ultrasonic transducer and said microcontroller being configured to determine whether said ultrasonic transducer is in contact with said fluid based on a signal level of said electrical signal, said frequency generator and said analyzing unit being arranged in said electronic housing.

20. The dry running detection system according to claim 19, wherein said pump assembly further comprises a motor, said motor comprising a motor housing, said motor housing being in contact with said pump housing and said electronic housing, said electronic housing being connected to one side of said motor housing, said fluid interior space surrounding said impeller interior space.

\* \* \* \* \*